US011404766B2

United States Patent
O'Driscoll et al.

(10) Patent No.: US 11,404,766 B2
(45) Date of Patent: Aug. 2, 2022

(54) WEARABLE ELECTRONIC DEVICE INCLUDING AN OVERLAPPING COMMUNICATIONS ANTENNA

(71) Applicant: Verily Life Sciences LLC, South San Francisco, CA (US)

(72) Inventors: Stephen O'Driscoll, San Francisco, CA (US); Anil Kumar Ram Rakhyani, Union City, CA (US); Louis Jung, Foster City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 15 days.

(21) Appl. No.: 16/949,248

(22) Filed: Oct. 21, 2020

(65) Prior Publication Data

US 2021/0135344 A1 May 6, 2021

Related U.S. Application Data

(60) Provisional application No. 62/927,921, filed on Oct. 30, 2019.

(51) Int. Cl.
*H01Q 1/12* (2006.01)
*H01Q 1/27* (2006.01)
(Continued)

(52) U.S. Cl.
CPC ............... *H01Q 1/273* (2013.01); *H01Q 1/38* (2013.01); *H01Q 7/00* (2013.01); *H01Q 9/16* (2013.01);
(Continued)

(58) Field of Classification Search
CPC ............ H01Q 1/273; H01Q 1/38; H01Q 7/00; H01Q 9/16; H01Q 13/10; H01Q 1/22; H01Q 1/24
See application file for complete search history.

(56) References Cited

U.S. PATENT DOCUMENTS 6,339,405 B1 1/2002 Gleener
6,342,868 B1 1/2002 Tsai et al.
(Continued)

OTHER PUBLICATIONS

International Application No. PCT/US2020/056875, "Invitation to Pay Additional Fees and, Where Applicable, Protest fee", dated Dec. 10, 2020, 2 pages.
(Continued)

*Primary Examiner* — Joseph J Lauture
(74) *Attorney, Agent, or Firm* — Kilpatrick Townsend & Stockton LLP

(57) ABSTRACT

A wearable electronic device is described. The wearable electronic device includes two communications antennae. A first antenna of the two is a current-carrying antenna electrically and physically connected to a printed circuit board of the wearable electronic device and housed in a first portion of a housing that is configured for mounting on a person's skin. A second antenna of the two is a scatterer antenna physically connected to an interior surface of a second portion of the housing and configured to overlap a portion of the current-carrying antenna. The second portion of the housing faces away from the person's skin when the wearable device is mounted on the person's skin. Current from the current-carrying antenna is induced in the scatterer antenna to enable communications between the wearable electronic device and one or more other electronic devices.

35 Claims, 5 Drawing Sheets

(51) Int. Cl.
*H01Q 7/00* (2006.01)
*H01Q 1/38* (2006.01)
*H01Q 9/16* (2006.01)
H01Q 1/22 (2006.01)
H01Q 13/10 (2006.01)
H01Q 1/24 (2006.01)

(52) U.S. Cl.
CPC ............. *H01Q 1/22* (2013.01); *H01Q 1/24* (2013.01); *H01Q 13/10* (2013.01)

(56) References Cited

U.S. PATENT DOCUMENTS

| | | |
|---|---|---|
| 6,400,332 B1 | 6/2002 | Tsai et al. |
| 6,424,311 B1 | 7/2002 | Tsai et al. |
| 6,590,539 B2 | 7/2003 | Shinichi |
| 7,042,412 B2 | 5/2006 | Chuang |
| 7,432,816 B1 | 10/2008 | Ku et al. |
| 9,825,363 B2 | 11/2017 | Ghabra et al. |
| 9,893,426 B2 | 2/2018 | Lapushin |
| 10,033,100 B1 | 7/2018 | Chayat et al. |
| 10,355,344 B1 * | 7/2019 | Ruaro .................... H04B 1/40 |
| 2013/0229314 A1 | 9/2013 | Kuehler et al. |
| 2015/0015448 A1 | 1/2015 | Almog |
| 2017/0040694 A1 | 2/2017 | Singh et al. |
| 2019/0036212 A1 | 1/2019 | Lee et al. |

OTHER PUBLICATIONS

International Application No. PCT/US2020/056875, International Search Report and Written Opinion, dated Mar. 3, 2021, 14 pages.

* cited by examiner

WEARABLE ELECTRONIC DEVICE INCLUDING AN OVERLAPPING COMMUNICATIONS ANTENNA

CROSS-REFERENCE TO RELATED APPLICATIONS

This application claims priority to U.S. Provisional Patent Application No. 62/927,921, filed Oct. 30, 2019, titled "Wearable Electronic Device Including an Overlapping Communications Antenna," the entirety of which is hereby incorporated by reference.

BACKGROUND

Certain types of electronic devices are designed to be worn by users. For example, watches and some medical monitoring devices may be mounted against a person's skin during use. In some cases, these wearable devices may include one or more communications antennas for communicating with other electronic devices (e.g., a smartphone, programming controller, etc.) and/or for powering the wearable devices.

BRIEF SUMMARY

Various examples are described relating to wearable electronic devices, systems including wearable electronic devices, and methods for assembling and using wearable electronic devices.

One general aspect includes a wearable device that includes a first housing portion and a second housing portion, the first housing portion and the second housing portion configured to couple together to form at least part of a device housing. The wearable device also includes a printed circuit board physically coupled to the first housing portion and including a first communications antenna physically connected thereto. The wearable device also includes a battery electrically connected to the printed circuit board. The wearable device also includes a second communications antenna physically connected to the second housing portion and including a first part and a second part. The first part of the second communications antenna overlaps a portion of the battery and the second part of the second communications antenna overlaps a portion of the first communications antenna.

Another general aspect includes a device, including a first housing portion, and a second housing portion, the first housing portion and the second housing portion configured to couple together to form at least part of a device housing. The device also includes a substrate physically connected to the first housing portion and including a current-carrying communications antenna physically connected thereto. The device also includes a scatterer antenna physically connected to the second housing portion and including a first part and a second part. The first part of the scatterer antenna overlaps a portion of the substrate that excludes the current-carrying antenna, and the second part of the scatterer antenna overlaps a portion of the current-carrying antenna to define an electromagnetic coupling region. The current-carrying antenna is configured to electromagnetically couple with the scatterer antenna within the electromagnetic coupling region to induce an electrical current and create a radiating electromagnetic field.

Another general aspect includes a method of assembling a wearable device, the method including providing a first housing portion of a device housing, the first housing portion including a substrate to which is physically connected a first communications antenna. The method also includes providing a second housing portion of the device housing, the second housing portion including a second communications antenna physically connected thereto. The method also includes aligning the second housing portion with the first housing portion such that a first portion of the second communications antenna overlaps a portion of the second communications antenna and a second portion of the second communications antennas overlaps a portion of the substrate that excludes the second communications antenna. The method also includes physically connecting the second housing portion and the first housing portion.

Another general aspect includes a device, including supporting means for physically supporting a plurality of components of the device including at least a battery and sensing circuitry. The device also includes generating means for generating electrical signals received from the sensing circuitry. The device also includes current-carrying means for radiating an electromagnetic field including data signals based on the electrical signals. The device also includes radiating means positioned to at least partially overlap the current-carrying means, the radiating means for magnetically coupling with the current-carrying means to boost a range of the electromagnetic field. The device also includes enclosing means for enclosing the supporting means, the generating means, the current-carrying means, and the radiating means.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
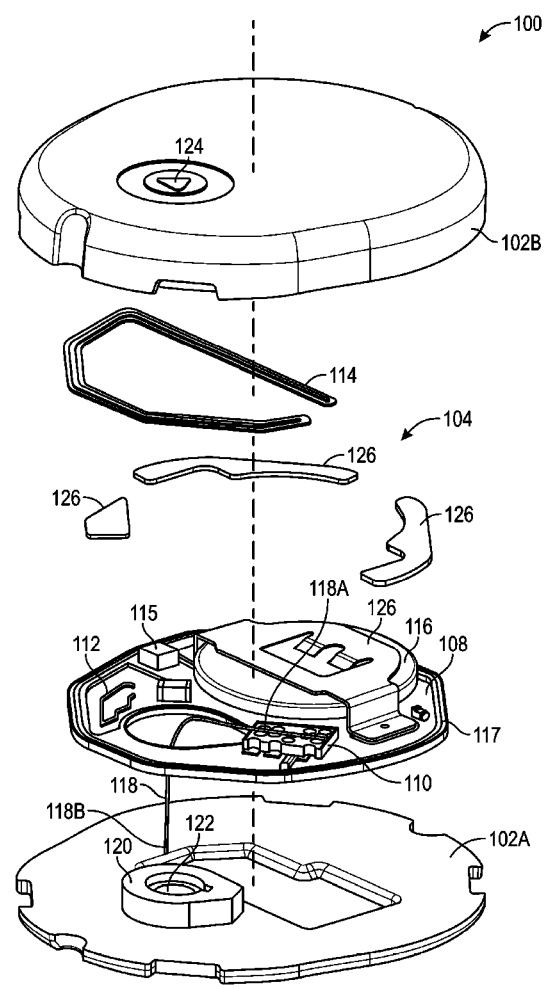
FIG. 1 illustrates an exploded perspective view of a wearable electronic device, according to at least one example.

Examples are described herein in the context of wearable electronic medical devices such as medical devices for continuous glucose monitoring ("CGM"). Those of ordinary skill in the art will realize that the following description is illustrative only and is not intended to be in any way limiting. For example, the features described with respect to wearable medical devices are applicable to any other electronic device that is held in close contact with a person's skin (e.g., watches, mobile phones such as smartphones, personal electronic devices, headphones, brain-computer interfaces, etc.). Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Because human tissue absorbs electromagnetic fields and because communications antennas in wearable devices are small, conventionally, designers of wearable electronic devices have placed the communications antennas as far away from the skin surface as possible. For example, a communications antenna of a wearable electronic device may be placed on an exterior surface of a housing of the electronic device. This may reduce the impact of the tissue absorbing the electromagnetic field produced by the communications antennas. In this arrangement, a connector is required to connect the communications antenna to a printed circuit board, which is typically included nearer the skin surface. This approach, however, may result in increased manufacturing costs and complexity due to the inclusion of the connector and potential for encapsulation of the antenna outside the device housing. Moreover, for some compact wearable devices, because the distance between the skin and the antenna is so small, this conventional approach may still result in an unsuitable amount of tissue absorption.

In an illustrative example, a wearable electronic device includes a housing formed from a bottom and a lid. The bottom has a smooth exterior surface for mounting against a person's skin. The interior of the bottom includes a printed circuit board to which is electrically and physically connected a current-carrying antenna (e.g., an on-PCB loop antenna). The lid is configured to couple with the bottom and includes a scatterer antenna (e.g., a compact half-wave length dipole scatterer) physically connected to an interior surface of the lid but physically separated from the current-carrying antenna by an air gap. The scatterer antenna is shaped such that a first part of the scatterer antenna sits above the current-carrying antenna and a second part of the scatterer antenna sits above a battery of the device. In operation, current from the current-carrying antenna is radiated through the scatterer antenna via the air gap. This arrangement of using the scatterer antenna in connection with the current-carrying antenna increases the overall separation between the primary radiating element (i.e., the scatterer antenna) and the person's skin, and does so without using a connector, which reduces cost and manufacturing complexity. Additionally, because the scatterer antenna is supported by the lid instead of being mounted to the printed circuit board in the bottom, space on the printed circuit board and within the device housing is conserved.

This illustrative example is given to introduce the reader to the general subject matter discussed herein and the disclosure is not limited to this example. The following sections describe various additional non-limiting examples of wearable electronic devices.

Referring now to the figures, FIG. 1 illustrates an exploded perspective view of a wearable electronic device 100, according to at least one example. The wearable electronic device 100 may be a wearable monitoring device that is mounted to a body at an exterior surface (e.g., against a person's skin), held against the body at the exterior surface, or mounted in any other suitable manner. As an example, the wearable electronic device 100 may be configured to monitor glucose levels of the person and communicate with a separate electronic device about the glucose levels.

The wearable electronic device 100 includes a first housing portion 102A (e.g., a lower housing portion), a second housing portion 102B (e.g., an upper housing portion), and a biosensor 104. The first housing portion 102A and the second housing portion 102B are configured to couple together to define a housing of the wearable electronic device. The second housing portion 102B includes a smooth exterior surface that faces outward from the person's skin. A smooth surface, free from sharp edges, may be desirable to decrease the potential for knocking the wearable electronic device 100 from the person's skin once mounted. For example, the wearable electronic device 100 may be worn under clothing (e.g., on the person's arm), and the smooth surface decreases the potential of the person's clothing snagging on the wearable electronic device 100.

The housing may be compact in size for placing on a person's skin. The housing may be made of any suitable material for housing the biosensor 104. Non-limiting examples of materials that may be suitable for the housing include silicone, polyethylene, polyvinyl chloride ("PVC"), polypropylene, nylon, polyurethane, polycarbonate, steel, aluminum, and other plastics and metals.

Figure 2:
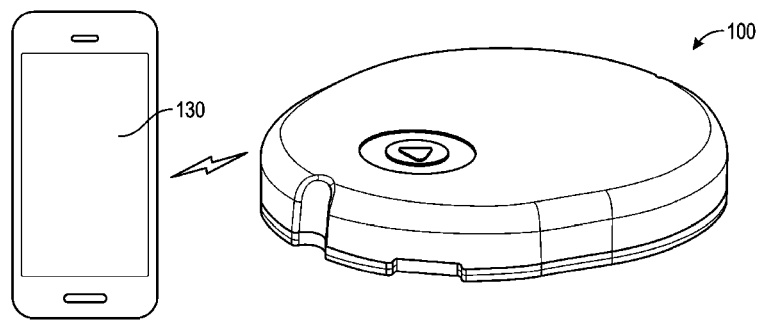
FIG. 2 illustrates a perspective view of the wearable electronic device of FIG. 1 in an assembled state, according to at least one example.

The first housing portion 102A may include a substantially planar surface to allow the wearable electronic device 100 to be placed against the person's skin. The wearable electronic device 100 may be secured to the skin using an adhesive, band, strap, or other securing means. In some examples, the wearable electronic device 100 may be worn for extended period of time (e.g., days, weeks, months, etc.). When assembled, a moisture barrier 128 (see FIG. 3) that extends between the housing portions 102 may create a seal that keeps moisture from infiltrating the biosensor 104. The seal may consist of an adhesive, elastomeric gasket, or other. When assembled, the second housing portion 102B encloses the biosensor 104 and mates with the first housing portion 102A (e.g., by way of a snap-fit, seal welded joint, or other). The second housing portion 102B may also be glued or otherwise bonded to the first housing portion 102A. FIG. 2 illustrates the wearable electronic device 100 after the first housing portion 102A and the second housing portion 102B have been mated together.

The biosensor 104, e.g., an analyte sensor, glucose sensor, or other electromechanical sensor for use in sensing biological information of a person, includes a printed circuit board ("PCB") 108 to which is physically and electrically connected a sensor carrier 110, a current-carrying antenna 112, sensing circuitry 115, a power source 116 such as a battery, and a near-field communication ("NFC") antenna 117. The biosensor 104 also includes a scatterer antenna 114.

The PCB 108 may be a rigid printed circuit board, a flexible printed circuit board ("FPCB"), or any other suitable substrate for electrically and physically connecting the components described herein.

The sensor carrier 110 is configured to support a sensor wire 118. The sensor wire 118 includes a proximal end portion 118A and a distal end portion 118B. The proximal end portion 118A is supported by the sensor carrier 110. For example, the proximal end portion 118A may be disposed within a groove or channel of the sensor carrier 110. The proximal end portion 118A is electrically connected to the PCB 108 via the sensor carrier 110. The sensor carrier 110 retains the proximal end portion 118A and a wire alignment structure 120 directs the distal end portion 118B via a first housing opening 122 in the first housing portion 102A. The wire alignment structure 120 may include a pair of tabs, a groove, or other structure capable of aligning the sensor wire 118 through the first housing opening 122. The wire alignment structure 120 can be a component that is attached to the PCB 108 or may be integrated into the construction of the first housing portion 102A (e.g., formed at the same time and using the same approach as was used to form the first housing portion 102A).

When in use, the distal end portion 118B, which includes one or more electrodes, is inserted into a person's skin to measure biological parameters (e.g., glucose levels) in the interstitial fluid of subcutaneous tissue beneath the skin. As illustrated, the wire alignment structure 120 is included on the PCB 108 at a position adjacent to the first housing opening 122. The second housing portion 102B includes a second housing opening 124 that is disposed above the first housing opening 122. Through the second housing opening 124 may be inserted an insertion needle to inject the distal end portion 118B of the sensor wire 118 underneath the person's skin. In some examples, the second housing opening 124 is formed from a deformable material that can reseal after the insertion needle has been inserted there through. In this manner, the sensor wire 118 can be injected without interrupting a moisture seal of the enclosure.

The current-carrying antenna 112 is a loop antenna that has been formed in the PCB 108. The current-carrying antenna 112 in combination with the scatterer antenna 114 may enable transmission of information from the wearable electronic device 100 (e.g., to one or more electronic devices). For example, as illustrated in FIG. 2, the wearable electronic device 100 may communicate over the air with a separate electronic device 130. To enable such communication, a transceiver, included in the sensing circuitry 115 or otherwise, may use the current-carrying antenna 112 to transmit real-time glucose readings monitored by the biosensor 104. The transceiver may also use the current-carrying antenna 112 to receive information from one or more other electronic devices (e.g., instructions to adjust settings of the biosensor 104, updates to software or firmware of the biosensor 104, etc.). In some examples, the antenna system including the current-carrying antenna 112 and the scatterer antenna 114 is configured to receive and send signals at 2.4 GHz, which may also correspond to the Bluetooth® standard for communication.

The scatterer antenna 114, which is connected to the second housing portion 102B, is any suitable communications antenna including a conductive trace antenna that is capable of scattering or otherwise amplifying electromagnetic waves from the current-carrying antenna 112. The scatterer antenna 114 is a half wavelength dipole antenna. Although, as described herein, the scatterer antenna 114 may also be a full dipole antenna and/or have other lengths ranging less than a half wavelength to greater than a full wavelength. Due to the compact size of the scatterer antenna 114 and its mounting location in the second housing portion 102B, a suitable separation distance between the primary radiating element of the antenna system (e.g., the scatterer antenna 114) and the human tissue is achieved. Additionally, because of these same reasons, the design of the wearable electronic device 100 is less restricted by the available space on the PCB 108.

The scatterer antenna 114 is connected to the second housing portion 102B and, at least a portion of which, is aligned with the current-carrying antenna 112. For example, when the wearable electronic device 100 is assembled, a portion of the scatterer antenna 114 overlaps (e.g., sits above) a portion of the current-carrying antenna 112 to define an overlap region. In some examples, an air gap may be present between the scatterer antenna 114 and the current-carrying antenna 112 in this overlap region. In this overlap region, the current-carrying antenna 112 magnetically couples with the scatterer antenna 114 to induce the current to create radiating electromagnetic fields from the scatterer antenna 114. In some examples, a spacing between the scatterer antenna 114 and the current-carrying antenna 112 in the overlap region may be about 1.9 mm. In some examples, the spacing is less than 1.9 mm or more than 1.9 mm (e.g., in range of about 0.5 mm to about 2.5 mm). The current-carrying antenna 112 may be oriented in a first plane and the scatterer antenna 114 may be oriented in a second plane that is substantially parallel to the first plane. In some examples, a substantial portion of the current-carrying antenna 112 may be oriented in the first plane and a substantial portion of the scatterer antenna 114 may be oriented in the second plane.

The scatterer antenna 114 may be formed from any suitable conductive material in any suitable manner. For example, the scatterer antenna 114 may include a metallic trace formed in a dielectric substrate such as a glass-reinforced epoxy laminate or a flexible printed circuit board. In some examples, the scatterer antenna 114 may include a high conductive copper trace having a thickness of 25-50 micrometers formed in the dielectric substrate. In this example, the scatterer antenna 114 may be physically connected to the second housing portion 102B using an adhesive 126. The adhesive 126 may be a pressure-sensitive adhesive ("PSA") applied before or after the scatterer antenna 114 has been brought into physical contact with the second housing portion 102B.

In some examples, the scatterer antenna 114 may be formed from a conductive ink deposited directly to the second housing portion 102B. For example, a silver ink trace having a thickness of 3-10 micrometers may be directly deposited on an interior surface of the second housing portion 102B.

The sensing circuitry 115 includes one or more electronic components configured for signal processing. For example, the sensing circuitry 115 may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, clocks, voltage regulators, and/or any other suitable component. The sensing circuitry 115 may be configured to receive electrical signals from the sensor wire 118 (e.g., via the PCB 108 and the sensor carrier 110) and process the electrical signals to determine glucose levels of the person.

In some examples, the sensing circuitry 115 includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from electrodes the sensor wire 118. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform the steps described herein as carried out, or assisted, by a processing device. Examples of computer-readable media may include, but are not limited to a memory chip, ROM, RAM, ASIC, or any other storage means from which a processing device can read or write information.

The near-field communication ("NFC") antenna 117 is any suitable antenna configured to enable near-filed communication between the wearable electronic device 100 and one or more other electronic devices, such as the electronic device 130 or other electronic devices. In some examples, the circuitry of the wearable electronic device 100 may be configured to use the NFC antenna 117 is initiate an NFC communication. In some examples, the NFC antenna 117 is the target of an NFC communication. In this manner, the NFC antenna 117 may enable passive and/or active communication between the wearable electronic device 100 and other electronic devices.

The power source 116 is a battery. The height of the power source 116 and/or power source hold down 119 represents a top-most elevation of the PCB 108. As separation between the current-carrying antenna 112 and the scatterer antenna 114 are restricted by this elevation, the length and width of the scatterer antenna 114 may be adjusted to improve the radio communication. For example, the length of the scatterer antenna 114 may be around 42 mm. In some examples, the length of the scatterer antenna 42 may be more than 42 mm or less than 42 mm (e.g., within a range of 30 mm to 80 mm). Different lengths and shapes of the scatterer antenna 114 are illustrates in FIGS. 4A-4C. In some examples, a portion of the scatterer antenna 114 may be sandwiched against the power source 116 and/or the power source hold down 119 (which may be formed from a metallic material). Because of this, the current may also be induced in the power source 116. In other words, not only does the current-carrying antenna 112 induce current in the scatterer antenna 114, in some examples, the current-carrying antenna 112 also induces current in the power source 116 via the scatterer antenna 114.

Figure 3:
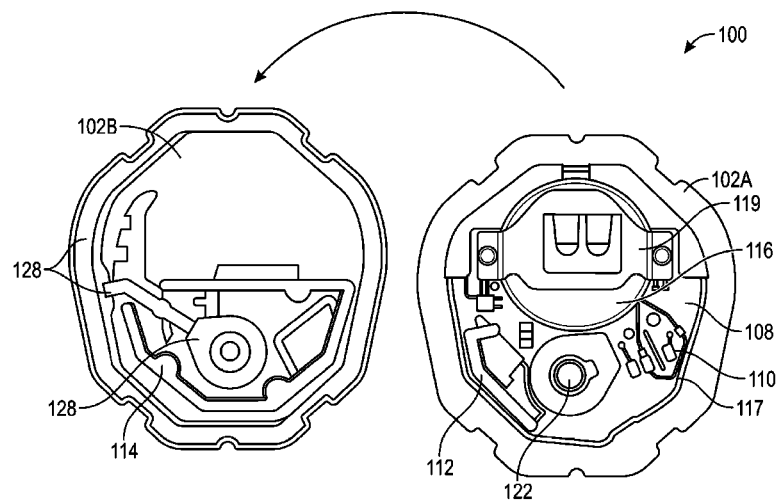
FIG. 3 illustrates a top view of a wearable electronic device with a device housing in an open state, according to at least one example.

FIG. 3 illustrates a top view of the wearable electronic device 100 with a device housing in an open state, according to at least one example. In FIG. 3, the second housing portion 102B has been removed from the first housing portion 102A to reveal contents of the device housing that are mounted or otherwise attached to the respective housing portions 102A, 102B.

In FIG. 3, the current-carrying antenna 112 is electrically and physically connected to the PCB 108 and the scatterer antenna 114 is physically connected to the second housing portion 102B. FIG. 3 also illustrates the moisture barrier 128 that, when assembled, extends between the housing portions 102 to create a seal that keeps moisture from infiltrating the biosensor 104. The moisture barrier 128 may include an adhesive, elastomeric gasket, or other suitable material.

Figure 4A:
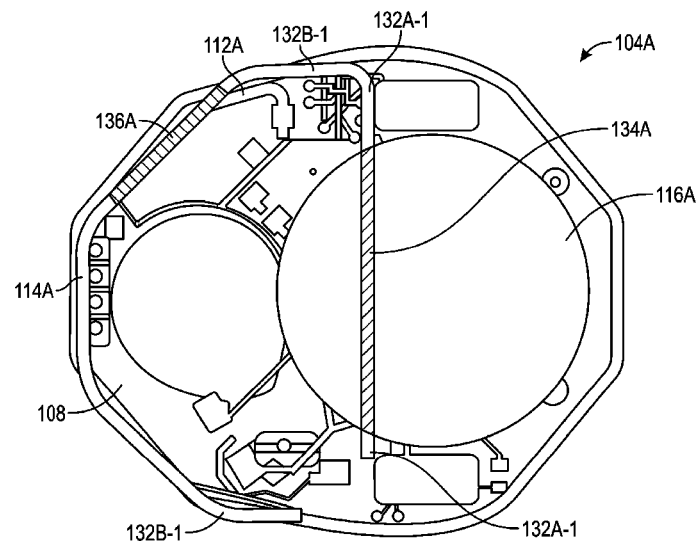
FIG. 4A illustrates a top view of a biosensor of a wearable electronic device including a scatterer antenna, according to at least one example.
Figure 4B:
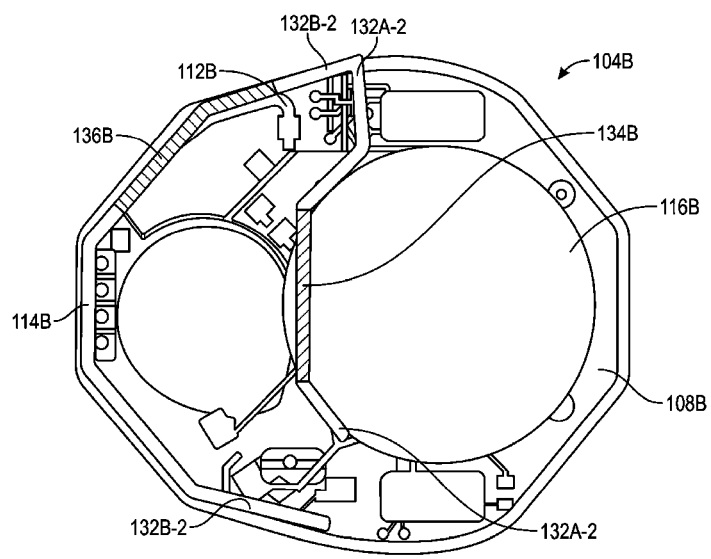
FIG. 4B illustrates a top view of a biosensor of a wearable electronic device including a scatterer antenna, according to at least one example.
Figure 4C:
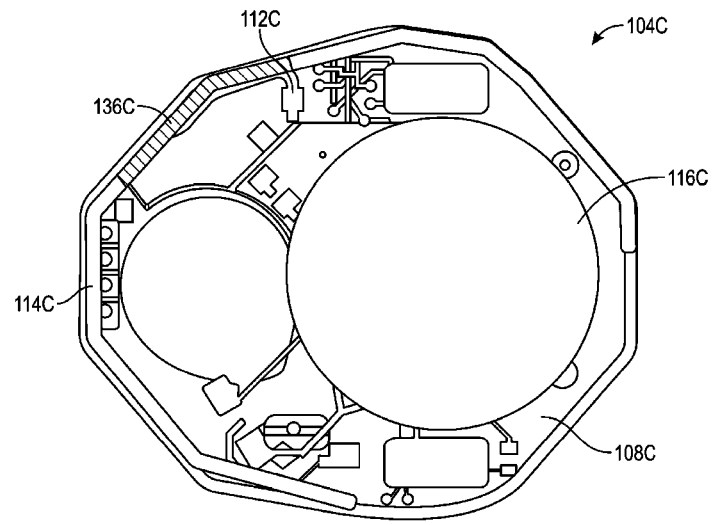
FIG. 4C illustrates a top view of a biosensor of a wearable electronic device including a scatterer antenna, according to at least one example.

Turning now to FIGS. 4A-4C, these figures illustrate a top view of the biosensor 104 of the wearable electronic device 100 including various designs of the scatterer antenna 114, according to various example. In FIG. 4A, the biosensor 104A includes the current-carrying antenna 112A, the power source 116A, and a scatterer antenna 114A that generally has an inverted "D" shape. In some examples, the scatterer antenna 114A may be a half wavelength dipole antenna.

The scatterer antenna 114A may be formed as one piece and include multiple integrally connected parts including at least a first part 132A-1 and a second part 132B-1. The first part 132A-1 overlaps (e.g., sits above) the power source 116A and includes a power source overlap region 134A. The second part 132B-1 has a generally arcuate shape and follows the perimeter region of the PCB 108a. An antenna overlap region 136A of the second part 132B-1 overlaps the current-carrying antenna 112A. In operation, the current-carrying antenna 112A induces a current in the scatterer antenna 114A in the antenna overlap region 136A. Because the power source 116A is metallic, the current also radiates outwards from the power source overlap region 134A.

In FIG. 4B, the biosensor 104B includes the current-carrying antenna 112B, the power source 116B, and a scatterer antenna 114B that generally has an inverted "D" shape with a reduced overlap the power source 116B as compared to the scatterer antenna 114A of FIG. 4A. In some examples, the scatterer antenna 114A may be a half wavelength dipole antenna.

The scatterer antenna 114B may be formed as one piece and include multiple integrally connected parts including at least a first part 132A-2 and a second part 132B-2. The first part 132A-2 overlaps the power source 116B and includes a power source overlap region 134B. The second part 132B-2 has a generally arcuate shape and follows the perimeter region of the PCB 108b. An antenna overlap region 136B of the second part 132B-2 overlaps the current-carrying antenna 112B. In operation, the current-carrying antenna 112B induces a current in the scatterer antenna 114B in the antenna overlap region 136B. Because the power source 116B is metallic, the current also radiates outwards from the power source overlap region 134B.

In FIG. 4C, the biosensor 104C includes the current-carrying antenna 112C, the power source 116C, and a scatterer antenna 114C that generally has a tipped "C" shape. In some examples, the scatterer antenna 114C may be a half wavelength dipole antenna.

The scatterer antenna 114C may be formed as one piece and have a generally arcuate shape that follows the perimeter region of the PCB 108C. The scatterer antenna 114C also includes an antenna overlap region 136C that overlaps the current-carrying antenna 112C. In operation, the current-carrying antenna 112C induces a current in the scatterer antenna 114C in the antenna overlap region 136C.

Figure 4D:
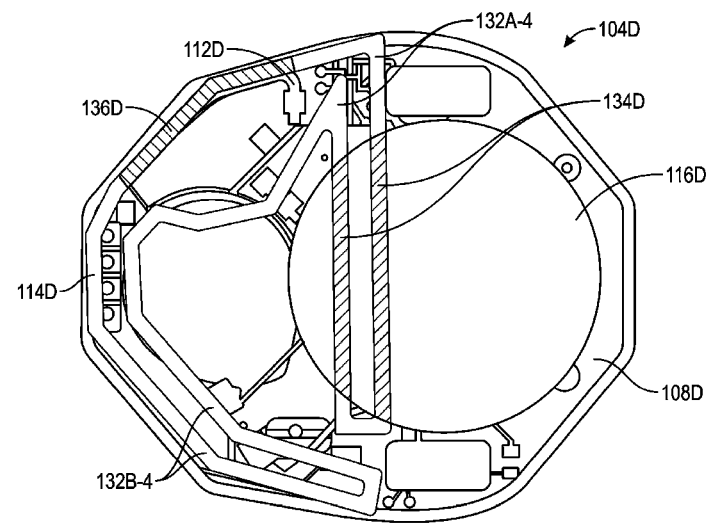
FIG. 4D illustrates a top view of a biosensor of a wearable electronic device including a scatterer antenna, according to at least one example.

In FIG. 4D, the biosensor 104D includes the current-carrying antenna 112D, the power source 116D, and a scatterer antenna 114D that generally has an inverted "D" shape that is a closed loop and results in a folded dipole antenna.

The scatterer antenna 114D may be formed as one piece and include multiple integrally connected parts including at least a first part 132A-4 and a second part 132B-4. The first part 132A-4 overlaps the power source 116D and includes a power source overlap region 134D. The second part 132B-4 has a generally arcuate shape and follows the perimeter region of the PCB 108D. An antenna overlap region 136D of the second part 132B-4 overlaps the current-carrying antenna 112D. In operation, the current-carrying antenna 112D induces a current in the scatterer antenna 114D in the antenna overlap region 136D. Because the power source 116D is metallic, the current also radiates outwards from the power source overlap region 134D.

Figure 5:
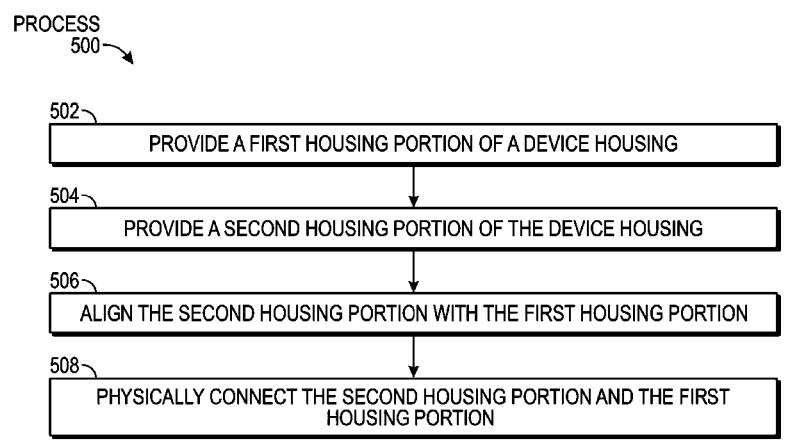
FIG. 5 illustrates a flow chart showing a process for assembling a wearable electronic device, according to at least one example.

FIG. 5 illustrates a flow chart showing a process 500 for assembling a wearable electronic device such as the wearable electronic device 100, according to at least one example. The process 500 begins at block 502 by providing a first housing portion of a device housing. The first housing portion may include a substrate to which is physically connected a first communications antenna. The substrate may be a printed circuit board. The first housing portion may be considered a lower housing portion and may be configured for mounting on a person's skin.

At block 504, the process 500 includes providing a second housing portion of the device housing. The second housing portion may include a second communications antenna physically connected thereto. For example, the second communications antenna may be printed on a flex PCB and connected to the second housing portion (e.g., at an interior surface of the second housing portion) or may be deposited as a conductive ink in the second housing portion.

At block 506, the process 500 includes aligning the second housing portion with the first housing portion. The two housing portions are aligned such that a first portion of the second communications antenna overlaps a portion of the second communications antenna and a second portion of the second communications antenna overlaps a portion of the substrate that excludes the second communications antenna. The proper alignment may be achieved using alignment tabs and grooves on the respective housing portions or in any other suitable manner.

In some examples, the substrate may include a battery physically connected thereto. In this example, the block 506 may further include aligning the second housing portion with the first housing portion such that the second portion of the second communications antenna overlaps at least a portion of the battery.

At block 508, the process 500 includes physically connecting the second housing portion and the first housing portion. This action may enclose the internal components of the wearable electronic device within the housing. Physically connecting may include press fitting, laser welding, gluing, or connecting in any other suitable manner.

In some examples, the process 500 further includes forming the second communications antenna. In some examples, forming the second communications antenna may include providing a metallic trace in a dielectric substrate. In some examples, forming the second communications antenna may include depositing a conductive ink onto an interior surface of the second housing portion.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:
1. A wearable device, comprising:
a first housing portion;
a second housing portion, the first housing portion and the second housing portion configured to couple together to form at least part of a device housing;

a printed circuit board physically coupled to the first housing portion and comprising a first communications antenna physically connected thereto;
a battery electrically connected to the printed circuit board; and
a second communications antenna physically connected to the second housing portion and comprising a first part and a second part, wherein the first part of the second communications antenna overlaps a portion of the battery and the second part of the second communications antenna overlaps a portion of the first communications antenna.

2. The wearable device of claim 1, wherein the second communications antenna comprises a half wave dipole antenna.

3. The wearable device of claim 1, wherein the wearable device is a continuous glucose monitoring device.

4. The wearable device of claim 1, wherein the first communications antenna is configured to electromagnetically couple with the second communications antenna to induce a current and create a radiating electromagnetic field.

5. The wearable device of claim 1, wherein the first communications antenna comprises an open-loop current carrying antenna.

6. The wearable device of claim 1, wherein the second communications antenna comprises a metallic trace formed in a dielectric substrate, and wherein the dielectric substrate is physically connected to the second housing portion.

7. The wearable device of claim 6, wherein the dielectric substrate comprises a glass-reinforced epoxy laminate material or a flexible printed circuit board.

8. The wearable device of claim 1, wherein the second communications antenna comprises a conductive ink that is deposited on the second housing portion.

9. The wearable device of claim 1, further comprising:
sensing circuitry comprising one or more electronic components electrically connected to the printed circuit board; and
a sensor wire that is electrically coupled with the sensing circuitry and comprises a distal end that, in a worn state in which the wearable device is worn by a person, extends to a position beyond an exterior surface of the first housing portion.

10. The wearable device of claim 9, wherein the wearable device is a wearable monitoring device and, when worn, the distal end of the sensor wire is positioned in tissue of the person to sense biological signals.

11. The wearable device of claim 1, wherein the first housing portion comprises an exterior surface for positioning the wearable device on skin of a person.

12. The wearable device of claim 1, wherein the second communications antenna is physically connected to the second housing portion via an adhesive material.

13. The wearable device of claim 1, wherein the first communications antenna is located in a first plane and the second communications antenna is located in a second plane that is different from the first plane and substantially parallel to the first plane.

14. The wearable device of claim 1, wherein the first communications antenna is configured to operate at a frequency between 2.4 and 2.5 gigahertz (GHz).

15. The wearable device of claim 1, wherein the first part of the second communications antenna comprises an arcuate profile and the second part of the second communications antenna comprises a straight profile.

16. The wearable device of claim 1, wherein the first part of the second communications antenna and the second part of the second communications antenna together define a D shape.

17. The wearable device of claim 1, wherein the second communications antenna comprises a full wave dipole antenna.

18. A device, comprising:
a first housing portion;
a second housing portion, the first housing portion and the second housing portion configured to couple together to form at least part of a device housing;
a substrate physically connected to the first housing portion and comprising a current-carrying communications antenna physically connected thereto; and
a scatterer antenna physically connected to the second housing portion and comprising a first part and a second part,
wherein the first part of the scatterer antenna overlaps a portion of the substrate that excludes the current-carrying communications antenna, and the second part of the scatterer antenna overlaps a portion of the current-carrying communications antenna to define an electromagnetic coupling region, and
wherein the current-carrying communications antenna is configured to electromagnetically couple with the scatterer antenna within the electromagnetic coupling region to induce an electrical current and create a radiating electromagnetic field.

19. The device of claim 18, further comprising a near-field antenna physically connected to the substrate within a perimeter region of the substrate.

20. The device of claim 19, wherein the current-carrying communications antenna is physically connected to the substrate closer to a center of the substrate than the nearfield antenna.

21. The device of claim 18, wherein the substrate comprises a printed circuit board.

22. The device of claim 18, further comprising a battery physically connected to the substrate, and wherein the first part of the scatterer antenna overlaps a portion of the battery.

23. The device of claim 18, wherein the scatterer antenna is formed from a continuous loop of conductive material.

24. The device of claim 18, wherein the device is configured to transmit data via the radiating electromagnetic field to an external electronic device.

25. The device of claim 18, wherein the current-carrying communications antenna operates in accordance with the Bluetooth standard.

26. The device of claim 18, wherein the scatterer antenna comprises a metallic trace that is formed in a dielectric substrate.

27. The device of claim 26, wherein the metallic trace is disposed on a first side of the dielectric substrate.

28. The device of claim 27, wherein the first side of the dielectric substrate is in physical contact with an interior surface of the second housing portion.

29. The device of claim 26, wherein the dielectric substrate comprises at least one of a glass-reinforced epoxy laminate material or a flexible printed circuit board.

30. A method of assembling a wearable device, the method comprising:
providing a first housing portion of a device housing, the first housing portion comprising a substrate that comprises a first substrate portion to which is physically connected a first communications antenna, and a second substrate portion that excludes the first communications antenna;
providing a second housing portion of the device housing, the second housing portion comprising a second communications antenna physically connected thereto;
aligning the second housing portion with the first housing portion such that a first portion of the second communications antenna overlaps a portion of the first communications antenna and a second portion of the second communications antenna overlaps the second substrate portion that excludes the first communications antenna; and physically connecting the second housing portion and the first housing portion.

31. The method of claim 30, wherein the substrate further comprises a battery physically connected thereto, and wherein aligning the second housing portion with the first housing portion comprises aligning second housing portion with the first housing portion such that the second portion of the second communications antenna overlaps at least a portion of the battery.

32. The method of claim 30, further comprising forming the second communications antenna.

33. The method of claim 32, wherein forming the second communications antenna comprises providing a metallic trace in a dielectric substrate.

34. The method of claim 32, wherein forming the second communications antenna comprised depositing a conductive ink onto an interior surface of the second housing portion.

35. A device, comprising:

supporting means for physically supporting a plurality of components of the device comprising at least a battery and sensing circuitry;

generating means for generating electrical signals received from the sensing circuitry;

current-carrying means for radiating an electromagnetic field including data signals based on the electrical signals;

radiating means positioned to at least partially overlap the current-carrying means, the radiating means for magnetically coupling with the current-carrying means to boost a range of the electromagnetic field; and enclosing means for enclosing the supporting means, the generating means, the current-carrying means, and the radiating means.

* * * * *